(12) United States Patent
Fishman

(10) Patent No.: US 6,537,587 B1
(45) Date of Patent: Mar. 25, 2003

(54) COMPOSITIONS CONTAINING MUSCLE-DERIVED ACTIVE AGENTS

(75) Inventor: Pnina Fishman, Herzliya (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 0 days.

(21) Appl. No.: 09/700,745

(22) PCT Filed: Jul. 6, 2000

(86) PCT No.: PCT/IL00/00395

§ 371 (c)(1),
(2), (4) Date: Aug. 28, 2001

(87) PCT Pub. No.: WO01/07060

PCT Pub. Date: Feb. 1, 2001

(30) Foreign Application Priority Data

Jul. 26, 1999 (IL) ................................................ 131096

(51) Int. Cl.⁷ .............................................. A61K 35/34
(52) U.S. Cl. ...................................................... 424/548
(58) Field of Search .......................................... 424/548

(56) References Cited

U.S. PATENT DOCUMENTS 4,576,696 A 3/1986 Oertli .......................... 210/641

FOREIGN PATENT DOCUMENTS

| EP | 0466440 A2 | 1/1992 |
|----|----|----|
| FR | 1957 M | 8/1963 |
| WO | WO 9609060 | 3/1996 |
| WO | WO 99/02143 | 1/1999 |
| WO | WO 01/07060 A1 | 2/2001 |

OTHER PUBLICATIONS

The Merck Manual of Diagnosis and Therapy, 16$^{th}$ Edition, Merck Research Laboratories, Rahway, NJ 1992, pp. 1819–1820.*

* cited by examiner

Primary Examiner—Jean C. Witz
(74) Attorney, Agent, or Firm—Birch, Stewart, Kolasch & Birch, LLP

(57) ABSTRACT

The present invention relates to a composition of matter having the following characteristics: (i) it is derived from muscle tissue; (ii) it filters through a filler with a maximal molecular weight cut-off of about 10,000 Dalton, preferably less than 3,000 Daltons; and (iii) it has a biological effect of inhibiting proliferation of tumor cells and stimulation of proliferation of leukocytes and neutrophils; and to a method for preparing said composition of matter.

Furthermore, the invention relates to pharmaceutical and neutraceutical preparations comprising the composition of matter disclosed herein. According to one embodiment, the pharmaceutical preparation is intended for treating or preventing cancer. The pharmaceutical preparations according to yet a further embodiment may be used for increasing the efficacy of a cytotoxic drug towards target cells, the target cells, being, for example, cancer cells. The pharmaceutical preparations may be administered parentally, however, are preferably administered orally.

5 Claims, 3 Drawing Sheets

COMPOSITIONS CONTAINING MUSCLE-DERIVED ACTIVE AGENTS

This application is the national phase under 35 U.S.C. § 371 of PCT International Application No. PCT/IL00/00393 which has an International filing date of Jul. 6, 2000, which designated the United States of America.

FIELD OF THE INVENTION

The present invention generally concerns a novel method for the production of a composition which inhibit growth of tumor cells and stimulates proliferation of normal cells. The invention further concerns the use of such a composition in the prevention and treatment of various malignant disorders and diseases, as well as in combination with chemotherapeutical treatments.

GLOSSARY

The following are terms which will be used throughout the description and claims and which should be understood in accordance with the invention to mean as follows:

Biologically active—having the following biological activities: inhibition of proliferation of tumor cells, stimulation of proliferation of leukocytes, mainly neutrophils, anti-metastatic effect in vivo and reduction of cytotoxic side effects of chemotherapeutic treatments.

Composition of matter—a composition comprising one or more substances each having one or more biological activities.

Muscle tissue—muscle tissue or cells obtained directly from an animal. For preparation of the biologically active composition from the muscle tissue or cells, the muscle tissue or cells may be used immediately after obtaining them from the animal or they may be maintained for various periods of time under conditions which enable, eventually, to prepare the composition of the invention therefrom.

Target cells—the cells affected by the composition.

Anti-metastatic effect—effect of preventing or reducing the metastatic process in a subject. The effect may be manifested in the prevention of appearance of metastatic foci, in a decrease in the rate of occurrence of metastatic tumors, or a decrease in the number of metastatic tumors appearing in the individual or in a decrease in the rate of cancer related mortality.

Chemoprotective effect—reduction of the cytotoxic side effect of chemotherapy and specifically of the reduction in the number of white blood cells and neutrophils in an individual treated with a chemotherapeutic treatment.

BACKGROUND OF THE INVENTION

Small molecules having a molecular weight of less than 3 kD and which inhibit the proliferation of various tumor cells were previously described in International Application Publication No. WO 96/09060. These molecules, termed "muscle factor" (NE), were shown, on the one hand, to have inhibitive activity on tumor cells and, on the other hand, to promote proliferation of non-tumor, normal cells such as fibroblasts and bone marrow cells in vitro. In addition the MFs where shown to exert a chemoprotective effect in vivo in that they decrease or prevent the reduction in the number of leukocytes and percentage of neutrophils in an individual receiving chemotherapeutic treatment. The MFs described above were produced from cultured medium of muscle cells or leukocytes grown in culture.

GENERAL DESCRIPTION OF THE INVENTION

In accordance with the present invention it was found that a very potent biologically active composition of matter may relatively easily be prepared in large quantities from muscle tissue obtained from various animal sources.

The present invention thus provides a method for preparing a biologically active composition of matter comprising:
(i) providing muscle tissue;
(ii) treating the tissue in a liquid medium under conditions in which said composition of matter contained within the tissue is freed into the medium as a supernatant;
(iii) separating the supernatant from cell matter; and
(iv) separating from the supernatant a fraction comprising substances having a molecular weight of below about 10,000 Dalton, preferably below about 3,000 Dalton said fraction being said biologically active composition of matter.

The muscle tissue from which the biologically active composition of matter of the invention is prepared may, for example, be chicken meat, may be turkey meat, beef, pork meat, etc. The biologically active composition of matter of the invention exerts its effect across species. Thus, for example, said composition of matter which is prepared from chicken muscle, will affect mammalian, including human target cells.

The composition of matter of the invention may be prepared from the muscle tissue immediately following the extraction of the muscle tissue from the animal. Alternatively, the extracted muscle tissue may be maintained for various periods of time following the extraction of the muscle tissue from the animal, under such conditions which will not bar the eventual preparation of the biologically active composition of matter therefrom. Such conditions may, for example, be storage in the cold, at times with a preservative. Furthermore, the meat may additionally be cooked, typically mildly, and stored for a period of time within the broth in which it was cooked. Such cooking, by itself, gives rise to release of the composition of matter to the surrounding medium and thus the broth, may also at times be used for the preparation of the inventive composition of matter.

The biologically active composition of matter obtained from muscle tissue may be in the form of a natural crude extract. The natural crude extract may be maintained in its original liquid form or may be dried, e.g. by lyophilization. In addition, the composition of matter of the invention may also be in the form of a purified extract. In order to obtain a more purified composition of matter, the fraction separated from the supernatant, as described above, may be subjected to additional purification steps such as, for example, fractionation by chromatography, typically high pressure liquid chromatography (HPLC), e.g. reverse phase HPLC. In addition, the original preparation may be subjected to additional filtration stages, may further be purified by dialysis, etc.

The biologically active composition of matter of the invention obtained by the above method was found to have several biological activities. First, the composition inhibits proliferation of malignant cells. Against this, the composition of matter of the invention does not inhibit proliferation of non-malignant cells and moreover, at times, stimulates proliferation of white blood cells, specifically neutrophils.

An additional biological activity of the composition of matter of the invention is its anti-metastatic effect in vivo. Administration of the composition of matter in a variety of animal models showed that it reduces the number of metastatic foci in the tested animals as compared to tumor-bearing animals which were not treated with the composition of matter of the invention.

In addition to the above activities, the composition of matter of the invention also has a chemo-protective effect in an individual receiving chemotherapeutic treatment. Such therapeutic treatments have severe cytotoxic side effects on a variety of cells including hematopoietic cells such as bone marrow cells, leukocytes, particularly neutrophils, and others. The composition of matter of the invention reduces or inhibits some of the toxic effects of such therapeutic treatments resulting in a more limited reduction in the number of the non-malignant leukocytes and, at times even an increase in the number of white blood cells, mainly neutrophils, in individuals receiving the composition of the invention in combination with the therapeutic treatment.

The composition of matter of the invention exerts its biological activity both when administered parenterally, as well as when administered orally. Oral administration of the composition of matter of the invention is a preferred mode of administration in accordance with the invention, as also noted below.

The present invention also provides a biologically active composition of matter having the following characteristics:
(i) it is derived from muscle tissue;
(ii) it filters through a filter with a maximal molecule weight cut-off of about 10,000 Daltons, preferably less than 3,000 Daltons;
(iii) it has a biological effect of inhibiting proliferation of tumor cells and stimulation of proliferation of leukocytes and neutrophils.

Preferably, said composition of matter also exhibits an anti-metastatic effect. Desirably, the inventive composition also inhibits a chemo-protective effect in an individual receiving chemotherapeutic treatment.

The present invention also provides a pharmaceutical or neutraceutical preparation comprising the composition of matter of the invention, as an active ingredient.

Also provided in accordance with the invention is a method of treatment or prevention of cancer or a method for inhibiting toxic side effects of chemotherapy, comprising administering to an individual in need an effective amount of the composition of matter of the invention.

The term "effective amount", as used herein, should be understood as an amount of the composition of matter of the invention which is sufficient to achieve a desired therapeutic effect.

Further provided by the invention is use of said composition of matter for the manufacture of a pharmaceutical or neutraceutical preparation.

The composition of matter of the invention may comprise one or more active substances each having one or more of the biological activities of the composition.

The biologically active composition of the invention has a low molecular weight and is soluble in water. The term "low molecular weight" should be understood as the molecular weight of a substance which filters through a filter having a maximal molecular weight cut-off of about 10,000 Daltons. Preferably the composition has a maximal molecular weight of 5,000 Daltons and most preferred the composition has a molecular weight of about 3,000 Daltons.

In accordance with one embodiment of the invention, the biologically active composition of matter of the invention is used for the treatment or prevention of cancer. For prevention of cancer, the composition of matter may be administered to individuals who do not have cancer and especially, to individuals having a high-risk of developing cancer. In this case, the composition of matter will typically be administered over an extended period of time in a single daily dose, in several doses a day, as a single dose and in several days, etc. For treatment of cancer, the composition of matter of the invention may be administered to individuals at various stages of cancer. Typically, the composition of matter will be administered as a follow-up of an initial treatment of the primary cancer, such as chemotherapy, radiation therapy or surgery for prevention of the development of metastatic tumors. However, the composition of matter of the invention may also be administered to an individual having an early stage cancer in order to reduce or prevent tumor growth.

The term "effective amount" in accordance with this embodiment will be an amount of the biologically active composition of matter in a given therapeutic regimen which is sufficient to inhibit or reduce the growth and proliferation of tumor cells. Where the composition of matter is administered for the treatment of cancer, the effective amount is an amount of said composition which will result, for example, in the arrest of growth of the primary tumor, in a decrease in the rate of occurrence of metastatic tumors, or a decrease in the number of metastatic tumors appearing in the individual or in a decrease in the rate of cancer related mortality. Wherein the composition is administered for cancer prevention, an effective amount will be an amount of said composition which is sufficient to inhibit or reduce the occurrence of primary tumors in the treated individual.

In accordance with another embodiment of the invention, the composition of matter is used to inhibit (i.e. prevent or reduce) some of the cytotoxic side effects of chemotherapeutic drugs. As mentioned above, the main cytotoxic effect of such drugs is the reduction in leukocyte counts, particularly in the neutrophils count in individuals receiving such treatment. The result of administration of the biologically active composition of matter of the invention in combination with such chemotherapeutic drugs is a more limited reduction in the number of neutrophils in the treated individual as compared to the number of such cells in a cancer-free individual and at times, even an increase in the number of these cells above normal levels.

In accordance with the latter embodiment, the term "effective amount" should be understood as meaning the amount of the biologically active composition of matter which protects an individual receiving chemotherapeutical treatments against the drug-induced reduction in the count of leukocytes, particularly neutrophils. Such an amount of the composition of matter may either increase the low number of such cells in a treated individual to restore them to the number of cells in a cancer-free individual or, at times, to increase the level of such cells even above the number of cells in a cancer free individual.

The composition of matter of the invention exhibits at times also a specific potentiating effect of the chemotherapeutic drug onto the cancer cells. Thus, in accordance with an embodiment of the invention, the composition of matter of the invention is used to increase the efficacy of a cytotoxic drug towards the cancer cells. This increase in efficacy may result in a more pronounced destruction of tumor cells at a given dose of the drug administered in combination with the composition of matter of the invention or in a reduction in the required dose of the drug needed to achieve a certain therapeutic effect when administered in combination with the composition of the invention. By this embodiment, the composition of matter of the invention is used to improve the therapeutic index of a chemotherapeutic drug. For the purpose of improving a therapeutic index of a chemotherapeutic drug, the effective amount of the biologically active composition of the invention will be an amount of the composition which either increases the cancer specific toxicity of the chemotherapeutic treatment or an amount of the composition which is effective in reducing the amount of the chemotherapeutic drug or drug combination required to achieve a desired effect of the chemotherapeutic drug or drug combination, i.e. reduction of the tumor load.

The composition of matter of the invention may be administered to an individual by any of the administration means known in the art. By one embodiment, in accordance with which a composition is formulated for parenteral administration (intravenous, intramuscular, subcutaneous or intraperitoneal administration), the composition is typically provided as a liquid mixture ready for use or, alternatively, as a powder or lyophilizate for mixing with a physiological liquid (e.g. saline) prior to use.

In accordance with another embodiment the pharmaceutical composition or preparation, comprising the biologically active composition of the invention is provided as an inhalable composition in the form of a spray or aerosol. The composition may also be provided in the form of a patch for transdermal administration.

In accordance with the invention, it was found that the biological activity of the composition of matter is exerted even when the composition is administered orally to the treated individual. Thus, by a preferred embodiment of the invention, the composition of matter is formulated for oral administration. Such formulations may be provided as a liquid, a powder or lyophilisate for mixing with the palatable liquid prior to administration, or it may be provided in a dosage form, e.g. in the form of a capsule or a pill.

The timing of administration of the biologic active composition of matter of the invention to an individual will depend on various factors and mainly on the specific desired effect in the treated individual. Thus, for example, where the composition is administered for prevention of cancer in an individual having a high-risk of developing cancer, a long-term treatment is desired. The composition may then be administered from the time at which the individual is defined as being in a high risk group and over an extended period of time, which may span the entire lifetime of the individual. Where the composition of the invention is administered to an individual having a primary cancer, typically the treatment will begin following treatment of the primary cancer by any acceptable means such as surgery, chemotherapy or radiotherapy. At times, the administration of the composition of matter of the invention may be desired prior to the beginning of such treatments or in combination with them. In case the composition of matter of the invention is administered to increase the therapeutic index of a chemotherapeutic drug, typically, the administration of the composition of matter of the invention may begin a period of time, e.g. several days, prior to the treatment with the chemotherapeutic drug and may then continue throughout the period of administration of the drug. At times, the administration of said composition of matter may proceed even after termination of the treatment with the cytotoxic drug. Furthermore, at times the onset of administration of the composition of matter may be after the beginning of treatment by the chemotherapeutic drug. During the period of combined administration of the composition of matter of the invention with the chemotherapeutic drug different regimes may be chosen. For example, the therapeutic drug and the composition of matter of the invention may be administered simultaneously at the same hours of day, they may be administered at different times of the day, they may be administered on different days, etc.

Where the composition of matter of the invention is intended to be administered to an individual in combination with a chemotherapeutic drug, the composition of matter may be combined into a single pharmaceutical formulation with the chemotherapeutic drugs.

The invention will now be illustrated by the following non-limiting examples with occasional reference to the attached figures.

DETAILED DESCRIPTION OF THE INVENTION

EXAMPLES

Materials and Methods

Figure 1:
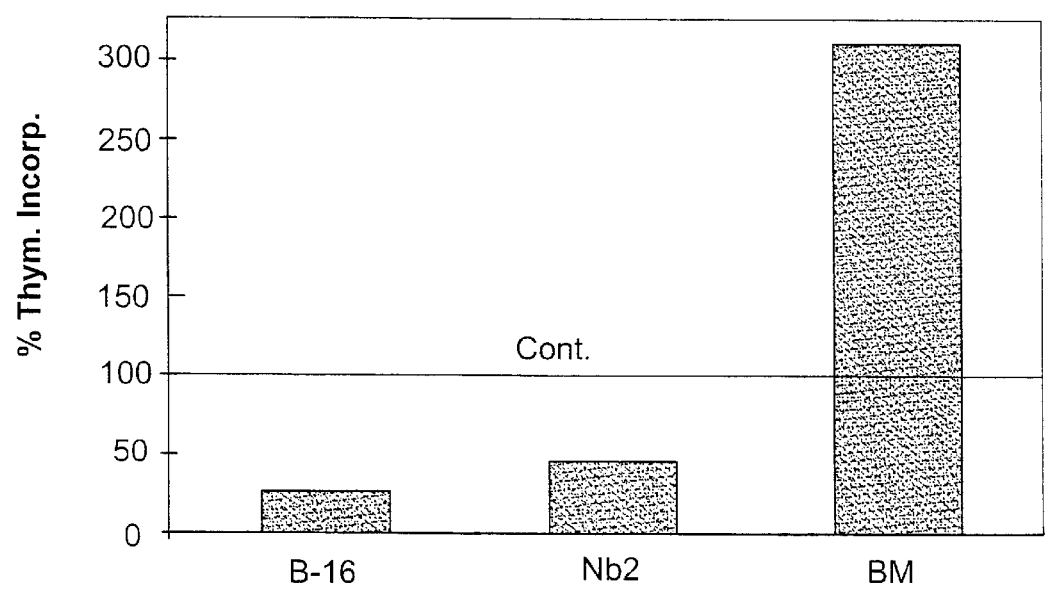
FIG. 1 is a schematic representation showing the incorporation of $[H^3]$-thymidine in tumor cells and bone marrow cells grown in culture in the presence of the biologically active composition of matter obtained from chicken muscle by the method of the present invention. Accordingly, the percentage from control of $[H^3]$-thymidine incorporation is denoted Thum. Incorp., control is denoted Cont. and bone marrow is denoted BM.

1. Preparation of the Biologically Active Composition From Chicken Muscle

Breast chicken muscle (50 gr), was dissolved in 150 ml water and was homogenized for 5 minutes in a blender. The whole homogenate was then transferred to 400 ml test tubes and was centrifuged in a refrigerated Sorvall centrifuge at 13,000 rpm for 20 minutes. The supernatant was filtered through 0.22-$\mu$m filter, and subjected to ultrafiltration through an Amicon membrane with a molecular weight cutoff of 3000 Dalton. This ultrafiltrated chicken homogenate will be referred to hereinafter as "biologically active composition".

2. Tumor and Normal Cells The rat lymphoma Nb2-11C growth hormone dependent cell line (Pines, M., Ashkenazi, A., Cohen-Chapnik, L., Binder, L., Gertler, *J Cellular Biochem.*, 37:119–129, 1988) and the B-16-F10 murine melanoma cell line were used. The cells were maintained in RPMI medium containing 10% FBS. Cells were transferred to a freshly prepared medium twice weekly.

Normal bone marrow cells were obtained from the C57BL/6J mice femur. Cells were disaggregated by passing them through a 25G needle.

3. Cell Proliferation Assays $[^3H]$-thymidine incorporation assay was used to evaluate cell growth. Tumor ($3 \times 10^3$/well) or bone marrow cells ($3 \times 10^5$/well) were incubated with 15% or 7.5% biologically active composition, in 96-well microtiter plates for 48 hours. RPMI medium and water, at the same concentration as was added for the biologically active composition, served as control.

A sample of the biologically active composition was boiled for 1 h and its effect on the proliferation of Nb2-11C lymphoma or murine bone marrow cells was examined.

During the last 18 h of incubation, each well was pulsed with 1 $\mu$Ci [$^3$H]-thymidine. Cells were harvested and the [$^3$H]-thymidine uptake was determined in an LKB liquid scintillation counter (LKB, Piscataway, NJ, USA).

One activity unit (AU) was defined as the amount of biologically active composition which exerted 50% proliferation inhibition of the Nb2-11C lymphoma cells in vitro.

4. Fractionation and Partial Purification of the Inhibitory Activity Found in the Biologically Active Composition HPLC separations: the biologically active composition was subjected to fractionation through two types of HPLC columns. During each purification step, fractions were collected and assayed for their ability to inhibit cell proliferation of Nb2-11C lymphoma cells. Each fraction was lyophilized prior to testing, suspended in RPMI medium and filtered through a 0.22 $\mu$m sterile filter.

The first column was a preparative Reverse Phase (RP) HPLC having the diameter of 2" and a length of 200 mm. The column was loaded with Merck Lichrosphere-C18 particles having a diameter of 12$\mu$ and a porosity of 60A. During each run, 800 ml of the above filtrate was loaded and the column was eluted with a gradient of acetonitrile at a rate of 2%/min, until reaching a level of 60% of acetonitrile. The rate of elution was 100 ml/min and 200 ml fractions were collected. A small portion (5 ml) from each fraction was dried and then used to test biological activity.

Active fractions were dried on a rotary evaporator, dissolved in 50 mM formic acid for the next chromatography step on a Polyhydroxyethyl A column (9.4×200 mm), 5$\mu$ (Poly LC, Columbia, Md.), with the eluent being a 50 mM formic acid solution. 200 $\mu$l samples were injected into the poly LC column and chromatographed at a flow rate of 0.5 ml/min and 0.5 ml fractions were collected. The fractions were dried in a concentrating centrifuge, and were tested for biological activity.

RESULTS

Example 1

In Vitro Effect of the Biologically Active Composition

The effect of the biologically active ingredient on the proliferation of rat lymphoma Nb2-11C and B-16-F10 murine melanoma cells grown in vitro was tested by adding the biologically active composition to cell cultures of the above two cells and comparing the proliferation of the cells (indicated by [H$^3$]-thymidine incorporation) as compared to the proliferation of the same cells grown in growth medium only. As seen in FIG. 1, the addition of the biologically active composition to cell cultures of Nb2-11C and B16-F10 resulted in reduced proliferation of these tumor cells.

The effect of the biologically active composition on bone marrow cells obtained from C57BL/6J mice femurs (as described above) was also tested by adding the biologically active composition to the bone marrow cells and comparing the proliferation of these cells to the proliferation of the same bone marrow cells grown in cell culture medium alone. As also seen in FIG. 1, the biologically active composition induced a substantive proliferative effect on bone marrow cells.

Example 2

Figure 2A:
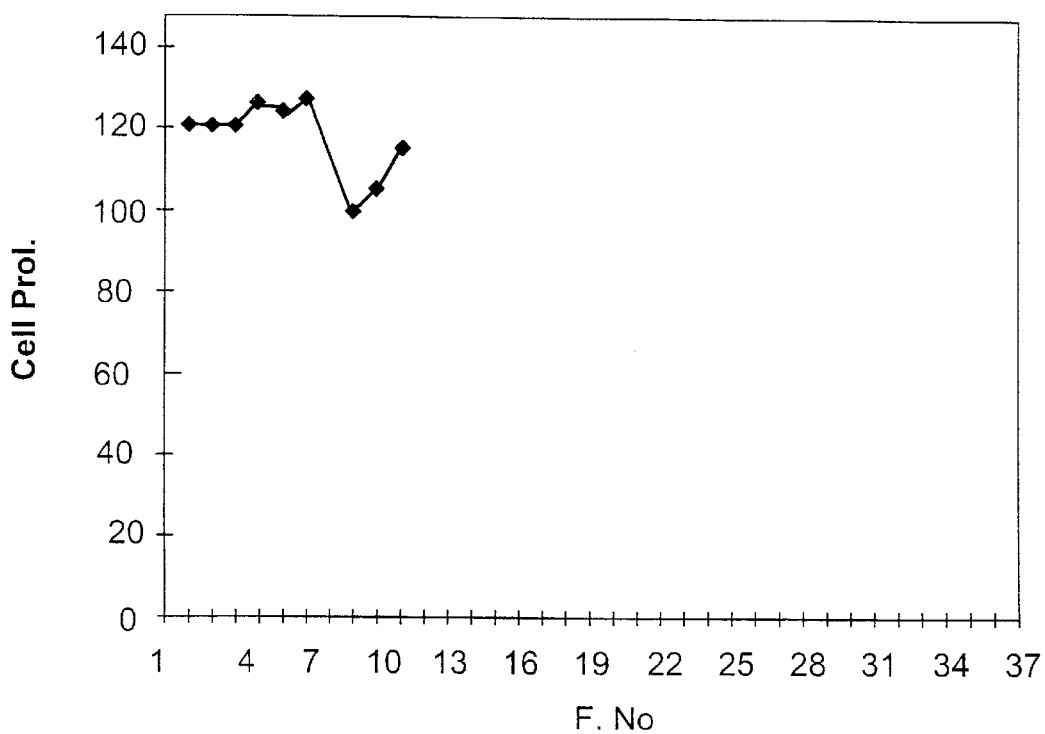
FIGS. 2A–2B are schematic representations showing the effect on proliferation of Nb2-11C lymphoma cells by fractions of the biologically active composition of matter obtained from chicken muscle after C-18 Reverse Phase HPLC (FIG. 2A) or after Polyhydroxyethyl A HPLC (FIG. 2B) columns. $[H^3]$-thymidine incorporation assay was used to determine inhibition of proliferation. Accordingly, the percentage of control of cell proliferation is denoted Cell Prol., and the Fraction No. is denoted F. No.
Figure 2B:
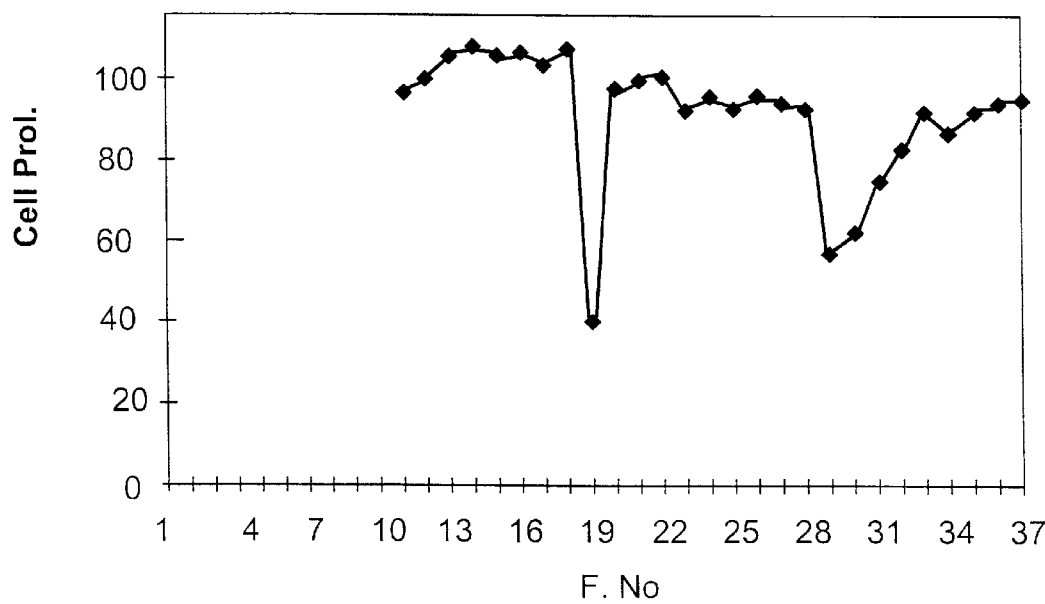

Fractionation and Purification of the Active Component in the Biologically Active Composition The biologically active compound was subjected to ultrafiltration through 3 kD Amicon membrane and was then fractionated through a RP-HPLC column and on a Polyhydroxyethyl A column as described above. The capability of various fractions eluted from the HPLC columns to inhibit proliferation of Nb2-11C lymphoma cells was tested. As seen in FIG. 2A, the inhibitory activity of the biologically active composition eluted on the RP-HPLC column was found as a single peak of activity at an acetonitrile concentration of 16%–20%. As seen in FIG. 2B, the inhibitory activity of the biologically active composition eluted on the Polyhydroxyethyl A column was detected in two peaks, one sharp peak at 18–20 min. and the second peak which was clear and broad eluted at 28–33 min.

Example 3

In Vivo Inhibition of Lung Metastasis in Mice by the Biologically Active Composition Mice inoculated intravenously (i.v.) with $2.5 \times 10^5$ B16-F10 melanoma cells were divided into the following two groups:

1. Mice which were treated orally twice daily with 4AU of the biologically active composition;
2. Mice treated orally twice daily with water (control vehicle).

The mice were sacrificed fifteen days after the beginning of the treatment, their lungs were removed and the black metastatic foci in the removed lungs were counted using a Dissecting Microscope.

Figure 3:
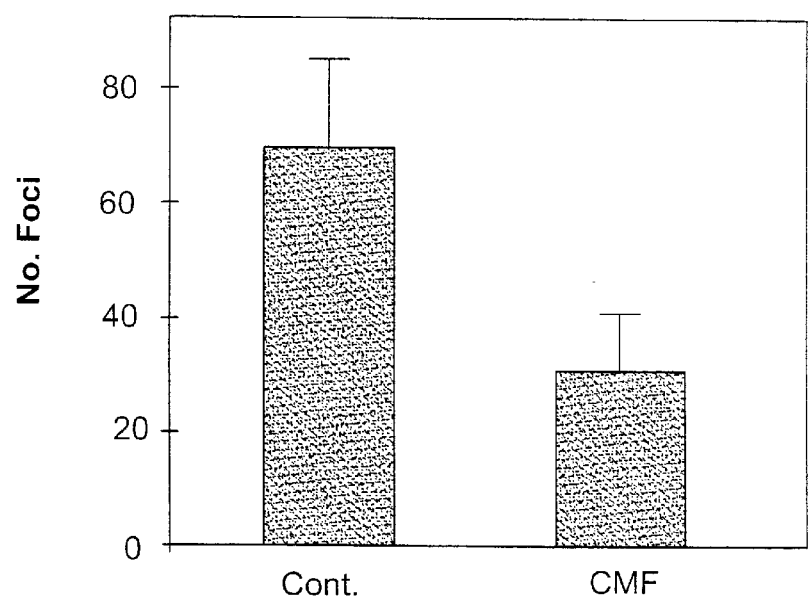
FIG. 3 is a schematic representation showing the number of lung metastases foci (No. Foci) in mice inoculated with B16-F10 melanoma cells and treated either with water (control, denoted by Cont.) or with the biologically active composition of matter obtained from chicken breast muscle.

As seen in FIG. 3, the number of metastatic melanoma foci in lungs of the mice treated with the biologically active composition was statistically significantly lower than the number of metastatic melanoma lung foci found in mice treated with water only.

Example 4

Myeloprotective Effect of the Biologically Active Composition on Mice Receiving Chemotherapeutic Treatment Mice were injected intraperitoneally (i.p.) with 50 mg/kg body weight of cyclophospharnide. The mice were then divided into the following three groups:

1. Mice receiving oral administration of 4AU of the biologically active composition 48 hrs and 72 hrs after treatment with cyclophosphamide;
2. Mice receiving cyclophosphamide only (control 1); and
3. An additional group of mice received oral administration of water only (control 2).

Ninety six hours after the beginning of receiving the above treatments, blood samples were taken from each of the treated mice. Blood cell counts were carried out in a Coulter counter and differential cell counts were performed on smear preparations stained with May-Grunvald-Giemsa solution.

Figure 4:
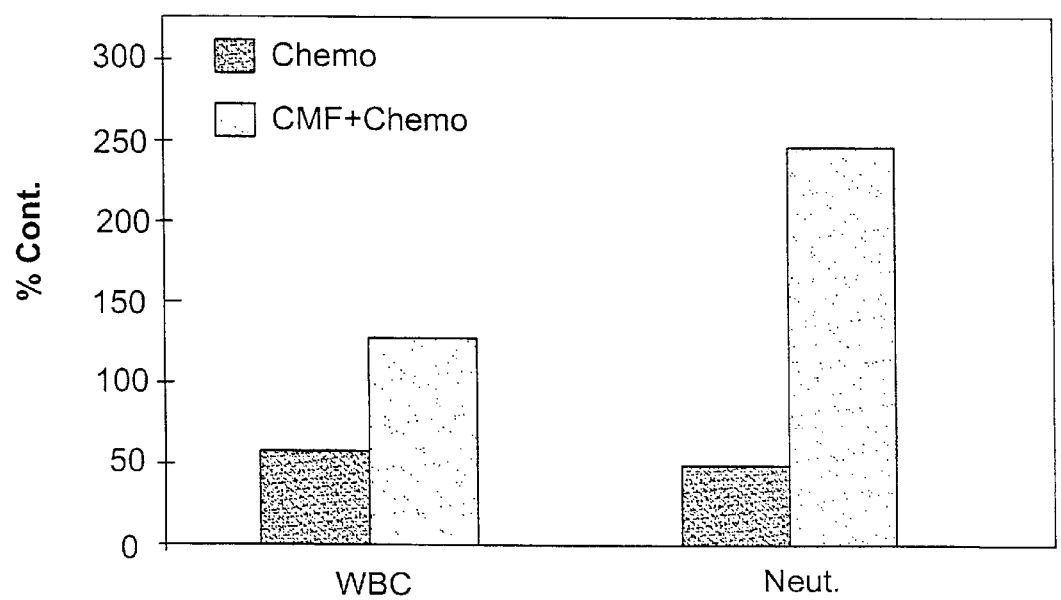
FIG. 4 is a schematic representation showing the level of white blood cells (WBC) and neutrophils (Neut.) in mice treated with chemotherapy alone (Chemo, black bars) or with the biologically active composition of matter following the chemotherapeutic treatment (CMF, gray bars).

As seen in FIG. 4, the number of peripheral blood leukocytes and neutrophils in mice receiving cyclophosphamide only (control 1) was reduced as compared to the number of these cells in mice which did not receive chemotherapeutic treatments (control 2). In mice receiving the biologically active composition following the cyclophosphamide treatment, the number of white blood cells was restored as compared to the mice receiving cyclophosphamide only (control 1), the number of the white blood cells and neutrophils being even higher than the number of the same cells in mice which did not receive cyclophosphamide at all (control 2).

What is claimed is:

1. A method for preparing a biologically active composition of matter from muscle tissue, comprising:
   (i) providing muscle tissue directly from an animal without prior culturing of said tissue;
   (ii) treating the tissue in a liquid medium under conditions in which said matter contained within the tissue is freed into the medium as a supernatant;
   (iii) separating the supernatant from cell matter;
   (iv) separating from the supernatant a fraction comprising substances having a molecular weight of below about 10,000 Dalton;
said fraction being said biologically active composition and having an anti-metastatic or a chemo-protective effect.

2. A method according to claim 1, wherein following step (iv), said fraction is further subjected to one or more additional purification steps.

3. A method according to claim 1, wherein step (iv) comprises separating from the supernatant a fraction having a molecular weight below about 3,000 Daltons.

4. A method according to claim 1, wherein the muscle tissue is obtained from chicken.

5. A method for inhibiting toxic effects of chemotherapy comprising administering to an individual receiving a chemotherapeutic treatment a biologically active composition of matter; said composition of matter having the following characteristics:
   (i) it is obtainable from within muscle tissue by extraction in a liquid medium;
   (ii) it filters through a filter with a maximal molecular weight cut-off of about 10,000 Dalton, or less;
   (iii) it has a biological effect of inhibiting proliferation of tumor cells and stimulating proliferation of leukocytes and neutrophils.

* * * * *